United States Patent [19]

Sonnerat et al.

[11] Patent Number: 4,842,605
[45] Date of Patent: Jun. 27, 1989

[54] HIP PROSTHESIS

[75] Inventors: Claude Sonnerat, Annecy-Le-Vieux; André Brunet, Maintenon, both of France

[73] Assignee: S.N.R. Roulements, Annecy Cedex, France

[21] Appl. No.: 34,417

[22] PCT Filed: Jul. 7, 1986

[86] PCT No.: PCT/FR86/00243
§ 371 Date: Mar. 6, 1987
§ 102(e) Date: Mar. 6, 1987

[30] Foreign Application Priority Data

Jul. 9, 1985 [FR] France .................. 85 10689

[51] Int. Cl.⁴ .............................. A61F 2/34
[52] U.S. Cl. ....................... 623/22; 623/18
[58] Field of Search ............ 403/127, 128, 131; 623/16–23

[56] References Cited

U.S. PATENT DOCUMENTS 2,396,137  3/1946  Venditty et al. ............ 403/127
3,683,421  8/1972  Martinie ..................... 623/22

FOREIGN PATENT DOCUMENTS 2646842  4/1978  Fed. Rep. of Germany ........ 623/23
2048698  3/1971  France ..................... 623/22
2060179  6/1971  France ..................... 623/22
2261743  9/1975  France ..................... 623/22
2357235  3/1978  France ..................... 623/22
2558053  7/1985  France .

Primary Examiner—Richard J. Apley
Assistant Examiner—David J. Isabella
Attorney, Agent, or Firm—Oblon, Spivak, McClelland, Maier, Neustadt

[57] ABSTRACT

The invention has as its object an improved hip prosthesis in which the femoral prosthesis oscillates around a pin inclined approximately 20° to the horizontal, characterized by the fact that this oscillation is provided inside the head of the femoral prosthesis by a double bearing comprising a row of rollers to support the radial loads and, a row of balls to support the axial loads.

6 Claims, 1 Drawing Sheet

HIP PROSTHESIS

BACKGROUND OF THE INVENTION

1. Field of the Invention

This invention relates to an improved hip prosthesis.

Total prostheses of the hip that are ordinarily made are the friction seat between the spherical part replacing the head of the femur and its housing implanted in the pelvis of the patient. Because of this friction and regardless of the materials used, a wear occurs that necessitates the replacement of all or part of the prosthesis at the end of a certain time.

To eliminate this drawback, French patent 2,261,743 describes a prosthesis whose oscillation pin mounted on a bearing is inclined 20° in relation to the horizontal, this arrangement making it possible during walking to have only a single oscillation movement around this pin and therefore to eliminate the wear between the spherical head and its housing since their relative movement then becomes zero.

However, if the friction between the spherical head and its housing has been eliminated, the problem has been shifted to the level of the bearing which is composed of a pin pivoting in a cylindrical housing and of a row of balls making possible the axial hold of the unit.

During the operation of the prosthesis, a wear by friction will develop between the pin and its housing necessitating, in time, a new operation.

SUMMARY OF THE INVENTION

This invention has as its object an improved hip prosthesis that totally eliminates said drawbacks.

Essentially for this purpose, the improved hip prosthesis according to the invention, in which the femoral prosthesis oscillates around a pin inclined approximately 20° to the horizontal, is characterized by the fact that this oscillation is provided inside the head of the femoral prosthesis by a double bearing comprising a row of rollers to support the radial loads and, a row of balls to support the axial loads, so that any movement of friction and therefore of wear is eliminated.

BRIEF DESCRIPTION OF THE DRAWINGS

Other characteristics and features of a hip prosthesis according to the invention will appear by way of example with reference to the accompanying drawing in which.

DETAILED DESCRIPTION OF THE PREFERRED EMBODIMENTS

Figure 1:
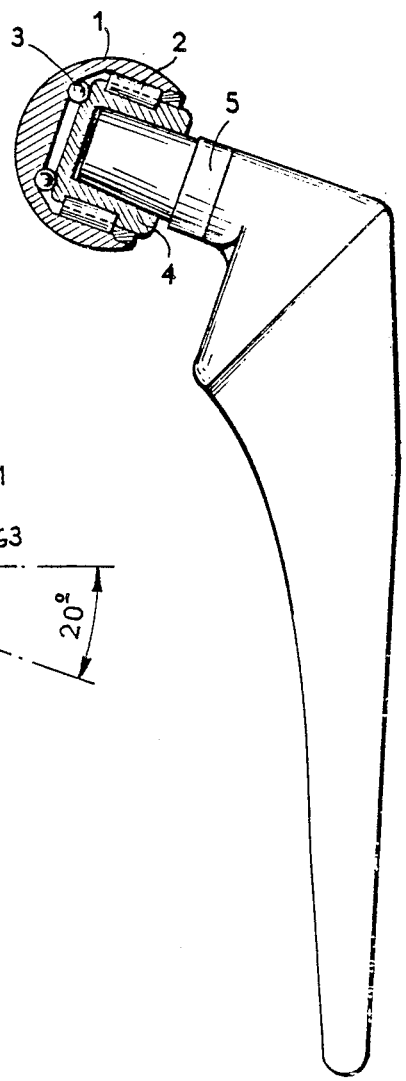
FIG. 1 is a view in axial section of a hip prosthesis according to the invention, seen in assembly position.

The hip prosthesis represented in FIG. 1 essentially comprises a spherical head 1 fitted on femoral support 5 which is implanted in the femur of the patient.

Spherical head 1 pivots inside a housing (not shown) implanted in the pelvis of the patient.

According to the invention, head 1 of the prosthesis comprises a bearing having a row of cylindrical rollers (2) and a bearing having a row of balls 3, making possible frictionless pivoting between outside ring or joint head 11, and inside ring or shell 4, of head 1 of the prosthesis, inside ring 4 being made solid with femoral support 5 by an assembly having a conical 44 (FIG. 2) or cylindrical 45 (FIG. 3) fit, or any other known fit for such assemblies (trigonal, grooves, etc.). The axes of the bore and ring 4 are coaxial and inclined approximately 20° to the horizontal.

Spherical outside ring 11 of head 1 of the prosthesis comprises in its bore a cylindrical race 12 in which first bearings in the form of rollers 2 travel to permit rotation and to support the radial loads, and a toric race 13 in approximately axial position in the bottom of its bore in which second bearings in the form of balls 3 travel to permit rotation and to support the axial loads which act on the prosthesis during walking.

In the same way, inside ring 4 possesses on its outside diameter a cylindrical race 42 to receive the row of rollers 2 and, on its bottom face, opposite the bottom of the bore of the outside ring, a toric race 43 to receive the row of balls 3. Shoulders 46 and 47 are provided on each side of race 42 to assure the axial guiding of rollers 2.

A cylindrical ring 6 is fitted by its outside diameter in the mouth of the bore head 1 of make the set of constituent elements 11, 2, 3, 4 of head 1 of the prosthesis so that they cannot be taken apart. This arrangement is made possible by the fact that ring 6 is either ferruled, or glued in its housing and, that its bore 63 is less than the diameter of race 12 and thus makes possible an axial hold of rollers 2. A clearance J is provided between rollers 2 and the face of ring 6, to avoid any friction during the operation of the prosthesis.

A sealing making it possible to avoid the pollution of the rollers by particles is assured by bore 61 of cylindrical ring 6 which is opposite the outside diameter of inside ring 4 by providing between these two parts a minimal clearance of operation.

Figure 3:
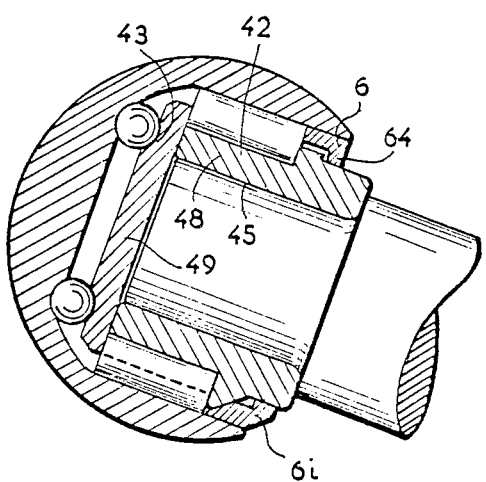
FIG. 3 is a view in axial section of the head of the prosthesis according to a variant embodiment.

According to another embodiment, cylindrical ring 6 is directly fitted into the extension of race 12 as indicated in FIG. 3.

The two rows of rollers 2 and 3 can be as shown with elements (rollers or balls) of contiguous bearings, or in a way known in the art, possess metal or plastic cages for separation of the rolling bodies.

Figure 2:
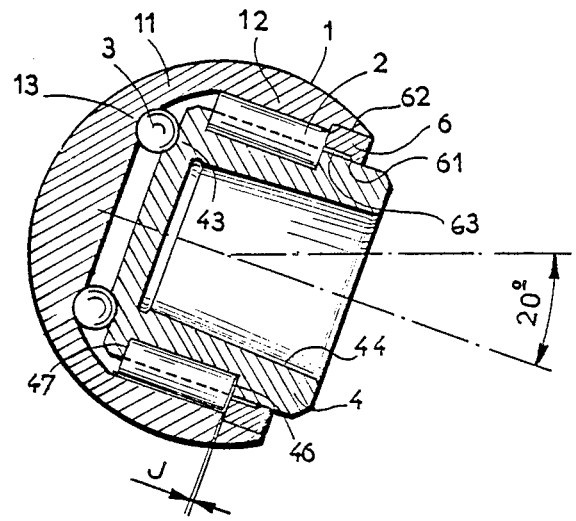
FIG. 2 is a view in axial section of the head of the prosthesis according to a first embodiment.

Inside ring 4 will be able to be either in a single unit as shown in FIG. 2, or in two parts 48 and 49 as shown in FIG. 3, to make possible a better distribution of the loads on each of the two rows of bearings. In this case, ring 6 will be able, for example, to comprise a radial flange 64 working with an inside recess of suitable shape of half-ring 48 to make it possible to hold the various parts that make up the head of the prosthesis during the assembly operations.

Of course, other variant embodiments can still be imagined without going outside the scope of the invention.

We claim:

1. A hip prosthesis comprising:
   a femoral member adapted to be implanted in a femur and an integral pin member extending from a proximal end of said femoral member at approximately an angle of 20 degrees to the horizontal;
   a joint head adapted to engage an acetabulum and rotatably connected to said pin so as to oscillate around said pin, said joint head comprising a substantially cylindrical bore defining a circumferential side wall and a bottom end wall; and
   a substantially cylindrical shell having a circumferentially outer wall and an outer end wall configured to engage said bore of the joint head and an inner bore to be affixed to said pin; and first bearings positioned between said circumferential outer wall of said shell and said circumferential side wall of said joint head, said first bearings comprising means for supporting said joint head for rotation about said pin and for supporting radial loads to said joint head; and second bearings positioned between said outer end wall of said shell and said bottom end wall of said joint head, said second bearings comprising means for supporting said joint head for rotation about said pin and for supporting the axial load to said joint head.

2. The hip prosthesis of claim 1 wherein said first bearings comprise cylindrical rollers.

3. The hip prosthesis of claim 1 wherein said second bearings comprise ball bearings.

4. The hip prosthesis of claim 1 including shoulders on said circumferential outer wall of said shell for limiting a race for said first bearings.

5. The hip prosthesis of claim 1 including a second ring fitted to a mouth of said bore of said joint head and comprising means for sealing said bore of said joint head and preventing separation of said joint head and said shell.

6. The hip prosthesis of claim 1 wherein said outer end wall of said shell is formed separate from said circumferential outer wall of said shell.

* * * * *